United States Patent [19]

Reinicke

[11] Patent Number: 4,820,273

[45] Date of Patent: Apr. 11, 1989

[54] IMPLANTABLE MEDICATION INFUSION DEVICE AND BOLUS GENERATOR THEREFOR

[75] Inventor: Robert H. Reinicke, Mission Viejo, Calif.

[73] Assignee: Eaton Corporation, Cleveland, Ohio

[21] Appl. No.: 162,766

[22] Filed: Mar. 1, 1988

[51] Int. Cl.$^4$ .............................................. A61M 5/00
[52] U.S. Cl. .................. 604/141; 604/891.1; 128/DIG. 12
[58] Field of Search ................... 604/67, 93, 141, 147, 604/153, 246, 890.1, 891.1; 128/DIG. 12

[56] References Cited

U.S. PATENT DOCUMENTS

| | | | |
|---|---|---|---|
| 3,527,220 | 9/1970 | Summers | 128/260 |
| 3,731,681 | 5/1973 | Blackshear et al. | |
| 3,894,538 | 7/1975 | Richter | 604/891.1 |
| 4,140,121 | 2/1979 | Kuhl et al. | 604/891.1 |
| 4,140,122 | 2/1979 | Kuhl et al. | 604/890.1 |
| 4,221,219 | 9/1980 | Tucker | 604/141 |
| 4,482,346 | 11/1984 | Reinicke | 604/152 |
| 4,486,190 | 12/1984 | Reinicke | 604/67 |
| 4,537,680 | 8/1985 | Barth | 210/316 |
| 4,557,726 | 12/1985 | Reinicke | 604/67 |
| 4,604,090 | 8/1986 | Reinicke | 604/118 |
| 4,626,244 | 12/1986 | Reinicke | 604/141 |
| 4,715,852 | 12/1987 | Reinicke et al. | 604/131 |
| 4,718,894 | 1/1988 | Lazorthes | 604/93 |

OTHER PUBLICATIONS

"A Portable Slow Infusion Capsule", B. M. Wright, The Journal of Physiology, Mar. 1965, vol. 177 (Cambridge University Press), pp. 5P & 6P.

"A Methodical Design Study of Miniature Perfusion Devices for Chemotherapy of Cancer of the Head and Neck", P. D. W. Soden, Masters Thesis, Manchester College of Science and Technology, Oct. 1965, pp. 65 and 66 and FIGS. 13, 15, 23 and 30.

Primary Examiner—Stephen C. Pellegrino
Attorney, Agent, or Firm—L. G. Vande Zande

[57] ABSTRACT

A flexible rubber bladder is disposed between a concave surface of a molded plastic base and a mirror image surface of a perforated molded plastic barrier, all enveloped by a molded plastic cover sealed to the base and defining a large volume cavity filled with inert gas under pressure. Injection of medication through a septum in the base fills a reservoir defined by the bladder and concave base surface and compresses the gas as the bladder moves to and against the barrier surface whereby the pressure exerted on the bladder forces medication through a metering outlet in the base and through an attached catheter to the infusion site. The free end of the catheter may be connected to a plastic protective cage for accumulating medication as droplets to dispense medication in bolus quantities.

30 Claims, 1 Drawing Sheet

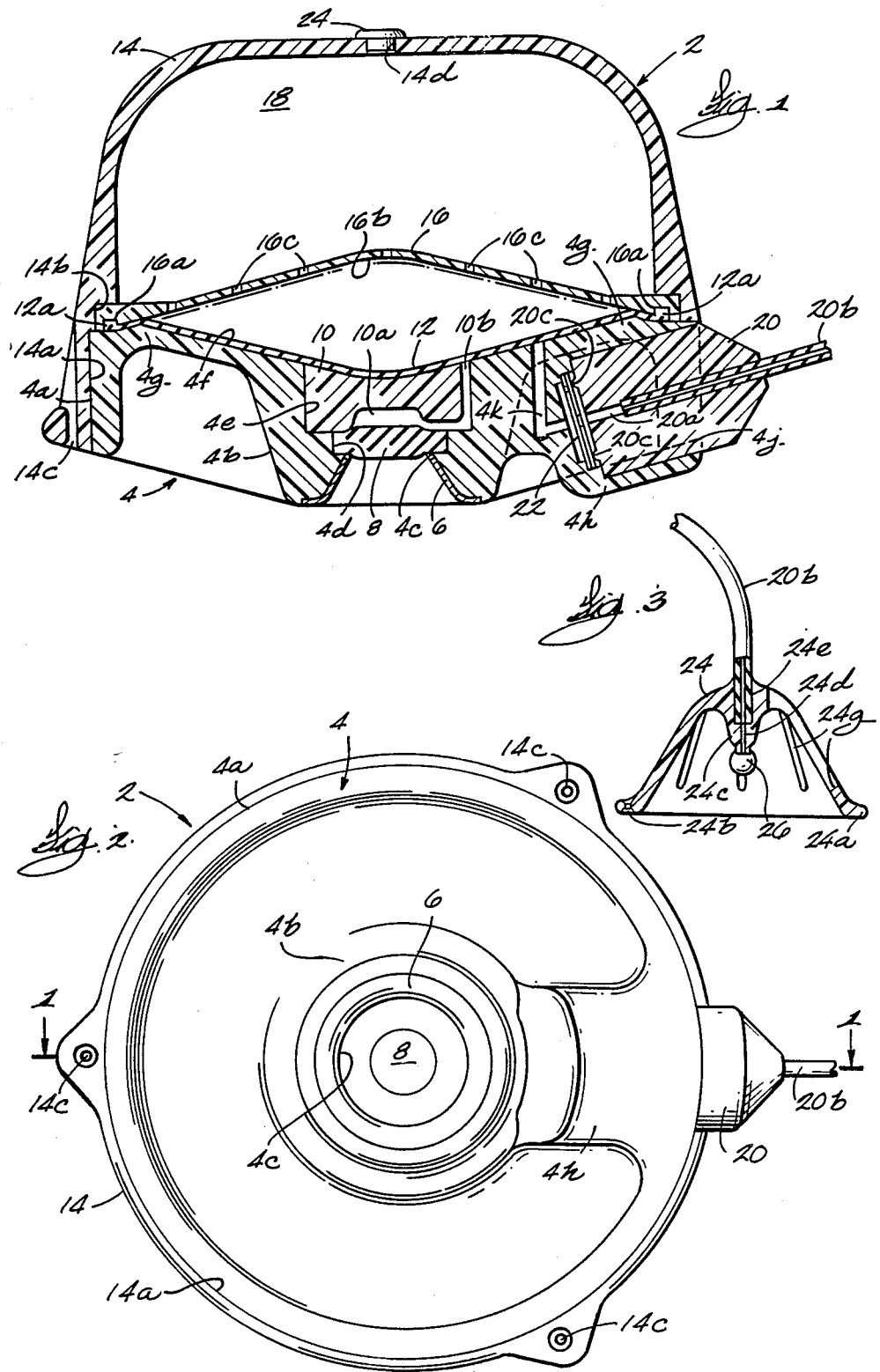

IMPLANTABLE MEDICATION INFUSION DEVICE AND BOLUS GENERATOR THEREFOR

BACKGROUND OF THE INVENTION

The present invention relates to implantable medication infusion devices and, more particularly to such devices which are arranged to provide a continuous unprogrammed flow of medication into the body. Still more particularly, the invention relates to devices of the aforementioned type which are particularly adapted to be implanted in farm animals such as cows or hogs and to a bolus generator used with such devices for periodically dispensing a bolus of medication.

An implantable medication infusion device of the continuous flow type is shown in my U.S. Pat. No. 4,626,244 issued Dec. 2, 1986. A relatively constant pressure is exerted on a diaphragm forming at least one wall of a reservoir containing medication. The pressure exerted on the diaphragm is above body pressure so that medication is forced out of the reservoir through a silicon substrate flow restriction device and a catheter to the infusion site within the body. That device is intended primarily for implantation in human bodies. Such devices are usually made particularly small and thin. Moreover, devices of the aforementioned type commonly use a two phase fluid (both gas and liquid coexisting at the fluid vapor pressure) such as Freon 11 produced by E. I. DuPont Co. or FC-87 or FC-88 Perfluorocarbon, produced by the 3M Company as the propellant for generating pressure on the diaphragm. These two phase fluids require the use of metal housing and reservoir parts for compatibility with the fluid. These and other factors to be considered in devices of the aforementioned type suitable for use in humans result in relatively high costs for the device.

It is known that infusion of growth hormones produced by recombinant DNA and possibly other drugs provide benefit in the animals such as an increased quantity of milk production in cows, larger growth of the animals to increase weight and edible meat, a reduced fat content of meat and an improved feed efficiency for the animals, among other things. Presently, such drugs are injected into the animals as often as once a day by syringe/needle bolus injection. Such procedures are time consuming and costly.

This invention provides an implantable device which can deliver a drug continuously or alternatively in a bolus fashion more than once a day for a prolonged period of time, requiring refill by percutaneous syringe/needle injection only once every several months. The device is made inexpensively of non-metallic materials and consists mainly of molded plastic and rubber parts. It is generally essential that such a device implanted in farm animals be inexpensive so that its cost does not offset the cost reduction effected by drug infusion. The device of this invention uses pressurized air or inert gas as the propellant acting upon the medication reservoir for forcing the drug out of the device to the infusion site. A silicon substrate flow restrictor is utilized to reduce the size and cost of this element. A fixed barrier is provided within the device to constrain an elastomer bladder forming a part of the medication reservoir against stretching, so as to eliminate added pressure on the drug which would be caused by contraction of the bladder if it were stretched. In certain drug applications, an efficacy improvement can be obtained when the drug is dispensed in repetitive boli rather than as a continuous flow. Previous devices have utilized electronically programmable electromagnetic pumps for generating periodic dosages of the drug. This invention provides a bolus generator having no moving parts which may be attached to the output end of a catheter for the device and located at the infusion site to dispense repeating boli of the drug.

The invention and its advantages will be more readily understood when reading the following description and claims in conjunction with the accompanying drawings.

BRIEF DESCRIPTION OF THE DRAWINGS

FIG. 1 is a cross sectional view of an implantable medication infusion device constructed in accordance with this invention taken along the line 1—1 in FIG. 2;

FIG. 2 is a bottom elevational view of the implantable medication fusion device of FIG. 1; and FIG. 3 is a cross sectional view of a bolus generator for the implantable medication infusion device of FIGS. 1 and 2.

DESCRIPTION OF THE PREFERRED EMBODIMENTS

FIGS. 1 and 2 of the drawing show the implantable medication infusion device 2 of this invention. The infusion device 2 has a generally cylindrically shaped main body portion 4 which has a straight sided outer cylindrical wall 4a. Main body 4 as a depending frusto-conically shaped boss 4b centrally located at its lower surface. A frusto-conically shaped recess 4c is formed concentrically within boss 4b and tapering in the reverse direction to the boss 4b. A cylindrical recess 4d is formed adjacent the inner end of recess 4c, the recess 4d having a larger diameter than the adjacent diameter of frusto-conical recess 4c to provide an annular shoulder along the upper end of the recess 4c. A second cylindrical recess 4e having a larger diameter than recess 4d is formed concentrically with the latter and is open to the upper surface 4f of main body 4. The upper surface 4f of main body 4 has a concave shallow conical shape. The outer periphery of upper surface 4f is relieved slightly to provide a shallow V-shaped annular projection 4g located inwardly from the outer periphery of main body 4. A semi-cylindrical boss 4h is formed radially on the under side of main body 4 as shown at the right of FIGS. 1 and 2. Boss 4h has a cylindrical bore 4j formed axially therein, the inner end of bore 4j being provided with a pair of concentric cylindrical recesses of progressively smaller diameters to provide annular stepped shoulders at the inner end of bore 4j. A passageway 4k communicates between the inner end of bore 4j and the upper surface 4f. A flanged frusto-conically shaped metal liner 6 is molded in place within recess 4c to serve as a guide for an injection needle as will be described later.

A disc-shaped silicone septum 8 is disposed in the recess 4d of main body 4 to extend across the inner opening of recess 4c. Septum 8 is somewhat thicker than the depth of recess 4d, therefor to be compressed along its periphery by a molded plastic needle stop 10 which is affixed within recess 4e by a solvent or ultrasonic weld bond. When so compressed, septum 8 forms a fluid-tight seal with main body 4. The upper surface of needle stop 10 is spherically concave to be tangentially continuous with upper surface 4f of main body 4. The lower surface of needle stop 10 has a recess 10a formed therein above septum 8. Needle stop 10 also has a radial groove 10b extending along the lower surface thereof from the recess 10a and then upwardly along one side thereof to the upper surface 4f of main body 4.

A molded rubber bladder 12 is positioned on the upper surface of main body 4. Bladder 12 is preformed to a shape which is complemental to upper surface 4f of main body 4 and the concave upper surface of needle stop 10 and is normally disposed in intimate contact with these surfaces. Bladder 12 has a molded annular bead 12a at its periphery for reasons to be described hereinafter.

A molded plastic cup-shaped cylindrical cover 14 open to its bottom end and having a straight side cylindrical counterbore 14a open to the bottom end thereof is assembled to the main body 4 such that the straight cylindrical surface 14a envelopes the complementally formed surface 4a. A second counterbore 14b, shallower and having a smaller diameter than counterbore 14a, is formed inwardly adjacent counterbore 14a. A molded plastic barrier 16 is disposed within the counterbore 14b to extend across the hollow interior of cover 14. Barrier 16 has an annular groove 16a formed in the underside thereof which receives annular bead 12a of bladder 12. Cover 14 and main body 4 are secured together in a compressed condition by a solvent or ultrasonic bond, thereby compressing bead 12a and the web of bladder 12 immediately adjacent bead 12a between main body upper surface 4f and barrier 16. When so assembled, the hollow interior of cover 14 and the upper surface 4f of main body 4 define a cavity 18 within the device. The lower periphery of cover 14 is provided with three apertures 14c spaced at 120° intervals to provide suture points for the housing when anchoring the device at an implantation site. Barrier 16 is a rigid dome-shaped member having a lower surface 16b which is formed as a mirror image to upper surface 4f inwardly of the projection 4g. Barrier 16 has a plurality of perforations 16c extending therethrough.

A catheter assembly comprising a cylindrical molded plug 20 having an axial aperture 20a extending therethrough is fixed to main body 4 within the cylindrical bore 4j. An elongated catheter tube 20b is affixed within the axial aperture 20a of plug 20.

A flow restrictor device 22 is disposed within the stepped recess at the inner end of bore 4j and is held in place by a raised annular sealing ring 20c formed on the inner end of plug 20. Flow restrictor device 22 is preferably formed on a silicon substrate and having a glass cover bonded thereto as disclosed in my aforementioned U.S. Pat. No. 4,626,244, the disclosure of which is incorporated herein by reference. As described in that patent, the flow restrictor may comprise a long capillary passageway therethrough having filter passages at each end, or may comprise a multiplicity of orifices arranged in a series. The flow restrictor device has an inlet passage communicating with passageway 4k and an outlet passage communicating with aperture 20a. Each version of the flow restrictor device 22 provides a predetermined resistance to the flow of liquid therethrough. The particular resistance can be precisely controlled by the cross sectional area of the capillary groove or the respective orifices to provide a predetermined fluid flow as a result of a predetermined pressure on said fluid.

When the device 2 is assembled as aforedescribed, the cavity 18 is filled with an inert gas such as gaseous nitrogen or air under pressure of approximately 10psig through an opening 14d in the upper wall of cover 14. A plug 24 is bonded within the opening 14d to seal the assembly. Bladder 12, being trapped between barrier 16 and upper surface 4f, seals the lower edge of cavity 18.

The pressure of gas within cavity 18 forces the bladder into continuous intimate contact with the upper surface 4f and upper surface of needle stop 10. The implantable medication infusion device 2 is surgically implanted within the body of the animal with the lower surface of main body 4 adjacent the skin of the animal, suturing through the apertures 14c to anchor the device. The depending boss 4b and the large, relatively steep walled recess 4c provide a readily detectable, large target area for injecting a medication into the device 2 through septum 8. A needle inserted through the skin of the animal is guided to the septum by metal liner 6. The needle extends through septum 8 into the recess 10a and is prevented from protruding further into the device by the needle stop 10. By depressing a plunger of a syringe connected to the needle, medication is injected through the needle into the recess 10a and passageway 10b between bladder 12 and upper surface 4f to force the bladder 12 upwardly toward under surface 16b of barrier 16. The space between bladder 12 and upper surface 4f of main body 4 provides a medication reservoir which has a volume capacity of approximately one-ninth the total volume of the cavity 18. That is, if the cavity 18 has a volume of 450ml, the medication reservoir capacity would be 50ml. As the medication reservoir fills, the bladder 12 reverses its shape and eventually is forced against the under surface 16b barrier 16. Barrier 16 serves to constrain bladder 12 over its total surface area, thereby preventing the bladder from stretching as a result of medication being injected into the reservoir. The filling of the reservoir compresses the inert gas within cavity 18 to increase the pressure within the cavity a small amount. The 10psig prevalent in the cavity 18 at the beginning of the filling operation is easily overcome by manual depression of the syringe during the filling operation. However, when the reservoir is full and bladder 12 is intimately in contact with the under surface 16b of barrier 16, a positive stop is provided for the medication reservoir, and the pressure on the medication is thereby transmitted back through the syringe to provide a positive feedback that the reservoir is full. The needle is then withdrawn from the device and from the animal and the septum 8 seals as the needle is withdrawn to prevent leakage of medication through the septum.

Pressure on the upper surface of bladder 12 through the perforations 16c of barrier 16 forces the medication out of device 2 through passageway 4k, the flow restrictor device 22, passageway 20c and the catheter 20b to the end of the catheter which is located at the infusion site within the animals' body. Due to the volume of the compressed inner gas within cavity 18, the pressure remains essentially constant throughout the dispensing period. Moreover, inasmuch as the bladder 12 is prevented from stretching, there is no contractive forces adding to the pressure on the medication which could tend to change the flow rate through the flow restrictor device.

It has been found that natural secretion of growth hormone (somatotropin) from the pituitary gland in the animals occurs in repeating boli. It follows that there may be an efficacy improvement when certain drugs, such as recombinant DNA produced growth hormones, are infused in repetitive boli rather than as continuous flow. A means of generating bolus formulations of the medication is shown in FIG. 3. A bell-shaped molded plastic cage 24 has an annular flange 24a along the lower open edge which has three apertures 24b (only one of which is shown) spaced at equal intervals around the periphery thereof for suture attachment thereof to the animal at the infusion site. The upper wall of cage 24 has an internal depending projection 24c in which is formed a passageway 24d which extends through the device. A counterbore 24e is formed in the upper surface of cage 24 coaxially with passage 24d. The opposite end of catheter 20b is affixed to the cage 24 within the opening 24e such that the passageway through the catheter aligns with the passage 24d in cage 24. The exterior surface of depending projection 24c is conically shaped and stepped to a reduced cylindrical diameter adjacent the bottom edge thereof to enhance the formation of medication as a droplet 26 thereon. To further enhance droplet formation, the distal end of projection 24c may be treated to be hydrophobic to the particular medication to be infused. Cage 24 is provided with a plurality of elongated apertures 24g formed therein.

The bolus generator is anchored at the infusion site to have an orientation as shown in the drawings wherein the passage 24d is oriented vertically to extend downward in the predominant position of the animal. Thus, under customary activity and position of the animal, a droplet of medication will form on the distal tip of depending projection 24c until such time as the mass of the droplet overcomes the adhesion factor thereof with the projection, thereby dropping off of the projection to be received in the tissue of the animal as a bolus dosage. The apertures 24g permit the passage of medication therethrough to the animal tissue in the event the position of the animal changes drastically from the predominant position. Although the apertures 24g are shown to be narrow with respect to the interposed webs, the proportions can readily be revised to provide narrow webs with wide apertures, thereby enhancing the flow of a droplet through the cage to the tissue.

The foregoing has described a preferred embodiment of an implantable medication infusion device particularly suited for use in farm animals. Costs are reduced by molding the major parts (main body 4, needle stop 10, cover 14, barrier 16, cage 24 and shell 26) of plastic, for example UDEL polysulfone available from AMOCO Performance Products, Inc. and by providing a molded rubber bladder 12 as the movable element of a medication reservoir. The bladder is preferably formed of Bromobutyl rubber produced by The West Company. The choice of materials is permitted by using inert gas under pressure as the propellant for the device. The bolus generator readily enables a continuous flow infusion device to be used as a bolus dispensing device. It is to be understood that the apparatus hereinabove described is but a single preferred embodiment and is susceptible of various modifications without departing from the scope of the appended claims.

I claim:

1. An implantable medication infusion device comprising:
   a housing comprising a main body, an interior cavity contiguous with said main body, and a fixed perforated barrier extending across said cavity in spaced relation to said main body;
   a flexible bladder disposed in said cavity between said barrier and said main body, said bladder being attached along its periphery to said housing forming with said main body a sealed medication reservoir and with a remaining portion of said cavity a pressure sealed chamber;
   pressurized inert gas in said chamber acting on said bladder forcing said bladder against said main body;
   a recess in an exterior surface of said main body;
   a passageway in said main body communicating between said recess and said reservoir;
   a penetrable self-sealing septum positioned in said housing adjacent said recess and closing off said passageway whereby said reservoir can be filled by injection through said septum, filling of said reservoir moving said bladder toward said barrier, thereby compressing said inert gas and increasing the pressure thereof, and abutment of said bladder against said barrier providing a positive limit to reservoir capacity; and
   flow restrictor means positioned in a recess in said main body, said flow restrictor means having an inlet connected to said reservoir, an outlet communicating with the exterior of said housing, and a flow restrictive passageway between said inlet and said outlet to limit flow of medication from said reservoir in response to pressure on said bladder to a predetermined rate.

2. The device of claim 1 wherein said bladder does not stretch during filling of said reservoir.

3. The device of claim 2 wherein said bladder is physically constrained by said main body and said barrier to prevent stretching of said bladder.

4. The device of claim 3 wherein said reservoir has a volume capacity approximately one-ninth the volume of said cavity.

5. The device of claim 1 wherein said bladder is preformed to a shape complemental to a surface of said main body contiguous with said cavity and is normally disposed in intimate contact with said surface.

6. The device of claim 5 wherein said bladder reverses its preformed shape during filling of said reservoir.

7. The device of claim 6 wherein said bladder is attached to said housing at the juncture of said barrier and said housing.

8. The device of claim 5 wherein said barrier comprises a stop surface for said bladder, said stop surface being formed as as mirror image of said main body surface.

9. The device of claim 8 wherein said main body surface and said barrier stop surface are substantially spherically concave having a greatest distance of separation at axial centers thereof.

10. The device of claim 9 wherein said bladder reverses its preformed shape during filling of said reservoir to be in intimate contact with said stop surface.

11. The device of claim 10 wherein said housing comprises a cup-shaped cover secured to said main body to provide said cavity.

12. The device of claim 11 wherein said barrier is trapped between said main body and said cover.

13. The device of claim 12 wherein said bladder has an enlarged peripheral bead received within a peripheral groove in said barrier, said bead being compressed against said main body when said cover is secured to said main body to form said sealed reservoir and sealed chamber.

14. The device of claim 1 wherein said housing is made of plastic material.

15. The device of claim 14 wherein the surface of said main body defining said recess is provided with a metal covering.

16. The device of claim 15 wherein said recess is frusto-conically shaped having a larger diameter at an exterior surface of said housing and a smaller diameter adjacent said septum.

17. The device of claim 16 wherein said recess is a relatively large and pronounced depression to provide a target area for injecting medication into said reservoir through said septum which may be readily detected through a skin covering said device.

18. The device of claim 17 wherein said exterior surface of said main body is relieved around an exterior rim of said frusto-conical recess to further enhance detectability of said target area.

19. The device of claim 1 further comprising needle stop means disposed in said main body between said septum and said reservoir in alignment with said recess blocking penetration of said bladder by a needle inserted through said septum.

20. The device of claim 1 wherein said flow restrictor means comprises a silicon substrate having a capillary groove formed in one surface thereof and connected between said inlet and said outlet, and a glass plate bonded to said surface of said silicon substrate to form with said substrate and flow restrictive passageway.

21. The device of claim 20 wherein said flow restrictor means also includes inlet filter means connected between said inlet and one end of said capillary groove, and outlet filter means connected between the other end of said capillary groove and said outlet.

22. The device of claim 1 wherein said flow restrictor means comprises a large number of serially connected orifices between said inlet and said outlet.

23. The device of claim 22 wherein said flow restrictor means comprises a silicon substrate having a large number of minute grooves formed in one surface thereof and serially interconnected along a predetermined flow path, and a glass plate bonded to said surface of said silicon substrate to form with said minute grooves a series of orifice type restrictions.

24. The device of claim 23 wherein said minute grooves are interconnected by troughs formed in said surface which are of a much greater depth than said minute grooves.

25. The device of claim 23 wherein said flow restrictor means also includes inlet filter means connected to one of said minute grooves at one end of said flow path.

26. The device of claim 25 wherein said flow restrictor means also includes outlet filter means connected to one of said minute grooves at the other end of said flow path.

27. The device of claim 1 further comprising a catheter attached to said outlet and a bolus generator attached to an output end of said catheter, said bolus generator comprising an apertured cage surrounding said output end having means affixing said output end in spaced relation to side walls of said cage and suture receiving means for anchoring said cage at a medication site wherein said output end is normally oriented vertically downward in a predominant position of the medication recipient whereby medication from said reservoir collects as a droplet on said output end and periodically falls therefrom as a bolus dispensed through said cage.

28. The device of claim 27 wherein said cage comprises a top wall having an internal depending projection in which said catheter output end is affixed, said projection having a passageway therethrough communicating with said output end and a particular external profile enhancing formation of droplets thereon.

29. The device of claim 28 wherein said suture receiving means comprises an annular external flange on said cage having apertures therethrough at spaced intervals.

30. The device of claim 28 wherein said external profile of said depending projection is made hydrophobic to the particular medication being infused.

* * * * *